United States Patent
Choudhary et al.

(10) Patent No.: US 9,714,912 B2
(45) Date of Patent: Jul. 25, 2017

(54) COMPOSITIONS FOR FABRIC BASED LATERAL FLOW ASSAY DEVICE USING ELECTROCHEMICAL DETECTION MEANS, AND DEVICES THEREFROM

(71) Applicant: ACHIRA LABS PVT. LTD., Bangalore (IN)

(72) Inventors: Tripurari Choudhary, Bihar (IN); K B Gururaj, Ranebennur (IN); Ashish Kumar Lal, Bangalore (IN); Manjunath Tahasildar, Karnataka (IN)

(73) Assignee: ACHIRA LABS PVT. LTD., Bangalore (IN)

( * ) Notice: Subject to any disclaimer, the term of this patent is extended or adjusted under 35 U.S.C. 154(b) by 191 days.

(21) Appl. No.: 14/421,406

(22) PCT Filed: Oct. 7, 2012

(86) PCT No.: PCT/IB2012/055410
§ 371 (c)(1),
(2) Date: Feb. 12, 2015

(87) PCT Pub. No.: WO2014/027225
PCT Pub. Date: Feb. 20, 2014

(65) Prior Publication Data
US 2015/0241379 A1    Aug. 27, 2015

(30) Foreign Application Priority Data

Aug. 13, 2012  (IN) ............................ 3356/CHE/2012

(51) Int. Cl.
*G01N 33/487* (2006.01)
*G01N 27/327* (2006.01)
(Continued)

(52) U.S. Cl.
CPC ......... *G01N 27/3275* (2013.01); *C12Q 1/002* (2013.01); *G01N 33/5438* (2013.01); *G01N 33/558* (2013.01)

(58) Field of Classification Search
CPC ...................................... G01N 27/327–27/3278
(Continued)

(56) References Cited

U.S. PATENT DOCUMENTS 4,774,039 A * 9/1988 Wrasidlo ............. B01D 61/145
210/500.34
5,863,400 A * 1/1999 Drummond ............ C12Q 1/004
204/192.17
(Continued)

FOREIGN PATENT DOCUMENTS

WO   WO 01/81915      11/2001
WO   WO 2009/121043   10/2009
(Continued)

*Primary Examiner* — Bach Dinh
(74) *Attorney, Agent, or Firm* — Seed IP Law Group LLP (57) ABSTRACT

The invention provides a composition for lateral flow assay device that comprises at least one fabric strand coated with a conducting material and a diagnostic material. The invention also provides a lateral flow assay device(10) having a proximal end(12), a distal end(14) and a testing zone intermediate between the proximal end(12) and the distal end (14). The lateral flow assay device(20) is made of a fabric comprising at least one strand(22) that defines a flow path. The at least one strand of the fabric in the testing zone is coated with a conducting material(24). The at least one strand is made of at least one of a cotton, a silk-based material, and combinations thereof. The invention also provides a lateral flow assay system(40) comprising the lateral flow assay device(42) of the invention, wherein the at least one electrode(52) connected to the strand(50) coated with (Continued)

the conducting material and measurement means(54) to measure the output from the at least one electrode(52).

19 Claims, 10 Drawing Sheets (51) Int. Cl.
*C12Q 1/00* (2006.01)
*G01N 33/543* (2006.01)
*G01N 33/558* (2006.01)

(58) Field of Classification Search
USPC .................................... 204/403.01–403.15
See application file for complete search history.

(56) References Cited

U.S. PATENT DOCUMENTS

2002/0148726 A1* 10/2002 Yamamoto ......... G01N 27/3272
   204/403.14
2007/0289880 A1* 12/2007 Zweig .................. C12Q 1/005
   205/777.5

FOREIGN PATENT DOCUMENTS

WO  WO 2012/004635   1/2012
WO  WO 2014/027225   2/2014

\* cited by examiner

Signature of Applicant

Rachna Singh Puri

Authorized Representative

COMPOSITIONS FOR FABRIC BASED LATERAL FLOW ASSAY DEVICE USING ELECTROCHEMICAL DETECTION MEANS, AND DEVICES THEREFROM

TECHNICAL FIELD

The invention relates generally to fabric based woven lateral flow assay devices comprising electrochemical detection means.

BACKGROUND

Lateral flow assay devices have been found to be a very convenient choice of device for many applications, especially in point-of-care diagnostics. Several different types of lateral flow assay devices are known in the art. Most lateral flow assay devices are made from a paper based or nitrocellulose based material to construct the device. More recently, fabric based lateral flow assay devices have garnered greater attention. For example, WO2009/121043 describes a cotton based lateral flow assay device. Reches et al (Reches et al, Applied Materials and Interfaces (2010), Vol. 2 No. 6, pp. 1722-1728) describe lateral flow assay devices based on cotton. In that report, the authors have attempted using the following materials as choice for lateral flow assay devices: nitrocellulose, cotton, polyester, nylon, natural silk, hemp, wool, acrylic fiber, a 50/50 blend of acrylic and cotton, and have categorically stated that the possible choices of material for a lateral flow assay device would be cotton, nylon and polyester, with cotton being the best and only choice for further studies.

WO2012/004635 and WO2012/004636 however describe the successful use of natural silk and appropriately treated silk as starting material for lateral flow assay devices.

This opens up the possibility for woven silk fibers to be used for such practical applications. Silk comprises a polypeptide chain obtained from natural sources and has been found to be biocompatible, and further comprises functional groups for any further modifications.

There is a need to develop the silk based lateral flow assay devices with a view to render it useful in a variety of test conditions for several different diagnostics testing situations.

BRIEF DESCRIPTION

In one aspect, the invention provides a diagnostic comprising at least one fabric strand coated with a conducting material and a diagnostic material.

In another aspect, the invention provides a lateral flow assay device having a proximal end, a distal end and a testing zone intermediate between the proximal end and the distal end, wherein the lateral flow assay device is made of a fabric comprising at least one strand to define a flow path, wherein the at least one strand of the fabric in the testing zone is coated with a conducting material, wherein the at least one strand is made of a silk-based material.

In yet another aspect, the invention provides a lateral flow assay system comprising the lateral flow assay device of the invention.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the term "or" is generally employed in its sense including "and/or" unless the content clearly dictates otherwise.

Strand as used herein refers to a single element (as a yarn or thread) of a woven or plaited material.

Analyte, as used herein, refers to a substance or chemical constituent that is determined in an analytical procedure. For instance, in an immunoassay, the analyte may be a protein ligand or a binder, while in blood glucose testing, the analyte is glucose. In one instance, the analyte could be a surface antigen that is a marker for the Hepatitis-B virus. In another exemplary instance, analyte may include a drug to be detected, such as cocaine from a blood analysis. The analytical procedure may include, for instance, fluorescence, mass-spectrometry, colorimetry, radio-imaging, electrochemical detection and the like, and combinations thereof. In some instances, analytes may refer to antibodies. In other instances, analytes may refer to antigens. In some other instances, analytes may include small molecule metabolites. Exemplary small molecule metabolites that are tested for diagnostic, therapeutic or other purposes include, but not limited to blood gas, metal and other non-metallic ions, electrolytes, other components like urea, creatinine, creatine etc., cells like CD-4 CD-8 that are useful as markers for viral load, and the like, and combinations thereof.

Antibody as used herein refers to protein that is used in the identification of specific antigen. The specific antigen is typically a marker of a disease or certain types of diseases. Sometimes, antibodies may also be referred to as immunoglobulins. Antibody may be primary or secondary antibody. Primary antibodies are antibodies raised against a specific antigen and are generally unlabelled. Primary antibodies may also be referred to as capture antibodies. Secondary antibody is an antibody that binds to primary antibody or fragments contained within the primary or capture antibody. Secondary antibody comprise label that render them useful for detection. Typical labels include fluorescence moiety, radio-active compounds, enzyme-linked labels, magnetically active particles, nanoparticles, quantum dots, latex particle labels, and the like, and combinations thereof. Depending on the label, the method used to detect, identify and quantitate may include fluorescence spectroscopy, radio-imaging, ELISA test and the like.

Antigen, as used herein, refers to a molecule that is recognized by an immune system of a living organism. Antigen also refers to molecular fragments that may be recognized by the immune system. It is generally known that a given antigen shows specificity to an antibody, and this property of an antigen is used in a variety of applications.

Silk as used herein refers to a fiber obtained from silkworms, more specifically from the larvae of mulberry silkworms. The silk most useful in the invention are those that can be woven into textiles, such as that obtained from the silkworm Bombyx Mori, however, other forms of silk that may be synthetically made or produced from other sources may also be used for this invention. Chemically, silk fiber comprises a chain of amino acids, which possesses functional groups. These functional groups may be used for binding useful moieties. As used herein, functional groups are reactive chemical moieties that can interact with other reactive species to form physical or chemical bonds.

Cotton as used herein refers to the cellulosic fiber made available from the genus Gossypium. It can be used as such, or may be modified to render some useful properties to the final fabric strand. Techniques and chemicals for the modification of naturally occurring cotton to improve its properties are known in the art. One exemplary process includes mercerization of cotton. Another process involves preparation of cellulose xanthate.

As noted herein, in one aspect the invention provides a diagnostic composition that comprises at least one fabric strand coated with a conducting material and a diagnostic material. In one embodiment, the at least one fabric strand is made of cotton. In another embodiment, the at least one fabric strand is made of silk. The silk may also be modified to suit the requirements of the device being fashioned. The modifications may include physical and chemical modifications. A particularly useful modification includes subjecting the silk fiber to a process of degumming. Methods and compositions for degumming are known in the art and can be suitably applied in the invention. Subsequently, the silk fiber may further be coated appropriately to render useful properties. Exemplary coatings include, for example, but not limited to, a surfactant, a hydrophilic coating, a hydrophobic coating, and the like, and so on. The choice of coating and the manner of applying the coating depends on various factors such as extent of hydrophilicity/ hydrophobicity, flow characteristics etc. and will become apparent to one skilled in the art.

The silk-based material may further comprise suitable modifications to enable its efficacy as a diagnostic composition. Thus, in an exemplary embodiment, the at least one strand of silk-based material comprises a suitable antibody for a specific antigen to detect the presence or absence of an analyte in the test sample. Methods of linking such antibodies to the silk based materials are known, and may include chemical and physical modifications.

Useful conducting materials in the invention include, for example, but not limited to, carbon ink, silver halide, gold, platinum, conducting polymers such as polyaniline, PEDOT/PSS, and the like, and combinations thereof. The conducting material, when it comes in contact with a specific material or types of materials, becomes electrically active giving rise to electric signals. These electric signals are then capable of being detected using appropriate detection means.

The diagnostic material useful in the invention may be any of the analytes described herein, or any reagent specific to a given analyte that can then be used to test the presence or absence of it, or alternately, measure the amount of the analyte present. The analyte or the specific reagent for the analyte is used to stimulate the conducting material upon contact giving rise to electric signals, which is then measured to provide a suitable output. In one specific embodiment, the diagnostic material is glucose oxidase, which when it comes in contact with glucose effects a redox reaction giving rise to an electron that leads to an electrical signal. The extent of the electrical signal may then be used to quantitate the amount of glucose present using a suitable predetermined calibration curve.

Figure 1:
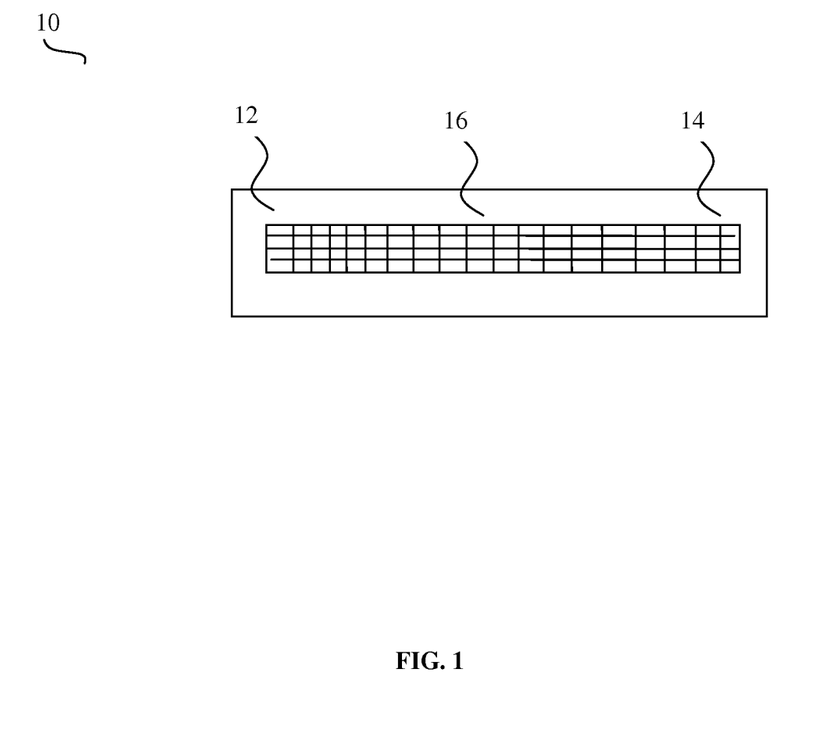
FIG. 1 shows a diagrammatic representation of an exemplary embodiment of the lateral flow assay device of the invention.

In another aspect, the invention provides a lateral flow assay device. FIG. 1 shows a diagrammatic representation of an exemplary embodiment of the lateral flow assay device of the invention generally represented by numeral 10. The device of the invention 10 comprises a proximal end depicted by numeral 12 in FIG. 1, a distal end 14 and a testing zone 16 that is present intermediate between the proximal end 12 and the distal end 14. The lateral flow assay device is made of a fabric comprising at least one strand that defines a flow path, shown in FIG. 1 by numeral 18. In one exemplary use case scenario, a sample is introduced onto the lateral flow assay device at the proximal end side of the device. Subsequently, the sample is allowed to flow along the flow path from the proximal end 12 to the distal end 14.

Figure 2:
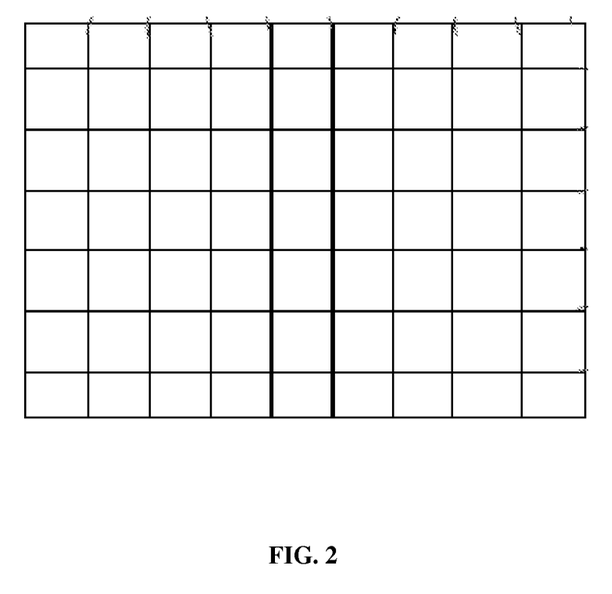
FIG. 2 shows a visual depiction of a plurality of strands woven together to form the lateral flow assay device of the invention.

The at least one strand of the fabric is made of a silk-based material. The silk as described herein may be used as such to form the lateral flow assay device of the invention. Methods of making the lateral flow assay device are described in the art, in for example, WO2012/004635 and WO2012/004636. One particularly useful method for making the device includes weaving a plurality of strands together. FIG. 2 shows a visual depiction of a plurality of strands woven together to form the lateral flow assay device of the invention.

The lateral flow assay device of the invention is made by the inter-weaving strands of the silk-based fiber. The method of inter-weaving is generally known among textile manufacturers. A useful method of inter-weaving includes the use of a double warp double weft technique. Other methods of introducing warp and weft are known in the art. Warp means the lengthwise yarns while weft means the yarn that is threaded through the warp. The patterning frequency of the warp and weft structure can influence the flow properties within the strands of fiber, and hence provides greater control over the use of the device of the invention. In addition, yarn properties such as ply, twists per inch and surface properties can also be used to tune wicking properties along the length of the fabric. Currently, machines exist that are used extensively in the textile manufacturing industry for the production of finished textile goods using the double warp double weft technique along with other techniques.

A loom is an exemplary device used for weaving, and may be advantageously used for the production of the diagnostic device of the invention. Several types of looms are readily commercially available for use. Exemplary looms useful in the invention include, but not limited to, jacquard loom, dobby loom, treadle loom, power loom, and the like.

The inter-weaving may also be effected using strands from different types of fibers. For example, a silk-based fiber may be interwoven with a cotton-based fiber. In another example, silk-based fiber may be interwoven with cotton-based fiber and a polyester-based fiber. Other useful fibers for the invention, include, for example, but not limited to, nylon, polypropylene, viscose, carbon fiber, graphene, and the like, and combinations thereof. In one particular embodiment, the silk-based fiber may be interwoven with a carbon fiber. Carbon fiber provides the advantage of being conducting in itself, and may or may not require any further process steps to render it more conducting. The relative amounts of each fiber used for preparing the final device depends on various factors such as strength, pliability, economics, and the like, and will become obvious to one skilled in the art. Lateral flow assay devices made by interweaving multiple types of fibers are described in, for example, international application PCT/IB2011/052753.

Figure 3:
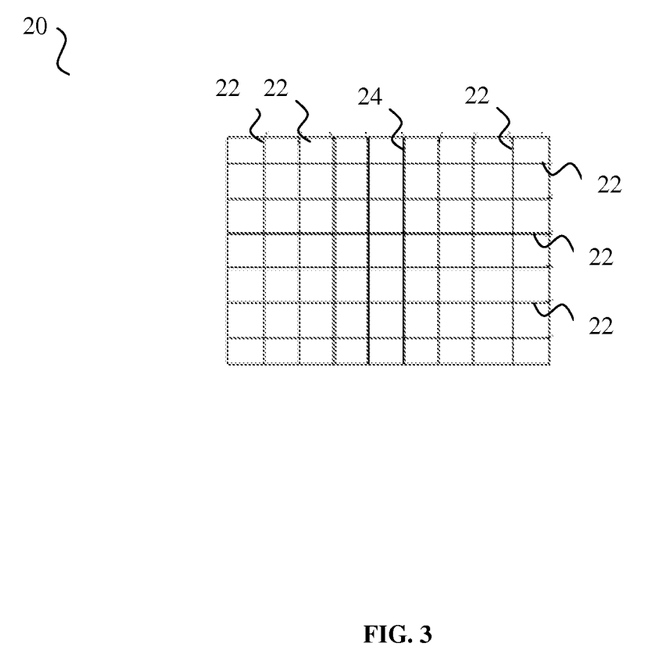
FIG. 3 shows an exemplary lateral flow assay device of the invention.

In the lateral flow assay device of the invention, the at least one strand in the testing zone is coated with a conducting material. The at least one fabric strand used for coating may be silk in one embodiment, and cotton in another embodiment. Useful conducting materials in the invention include, for example, but not limited to, carbon ink, silver halide, and the like, and combinations thereof. The conducting ink, when it comes in contact with a specific material or types of materials, becomes electrically active giving rise to electric signals. These electric signals are then capable of being detected using appropriate detection means. FIG. 3 shows an exemplary lateral flow assay device of the invention represented by numeral 20 made by weaving a plurality of strands 22. In this exemplary depiction, one strand is coated with a conducting material, shown by numeral 24. The at least one strand coated with a conducting material further comprises a reagent used for testing purposes. Such reagents include, for example a glucose oxidase, to enable the device for testing for blood glucose levels. Other materials may also be used to coat the at least one fabric strand that can facilitate electron transfer rendering the yarn electrically active. Such extraneous materials include, for example a mediator. A useful mediator material is potassium ferricyanide. As used herein, working electrode refers to the fabric strand that is coated with the conducting material and diagnostic material; a reference electrode refers to the fabric strand that is coated with the reference conducting material, and counter electrode refers to the fabric strand that is coated with the conducting material. The working electrode may further comprise a mediator in some instances.

Figure 4A:
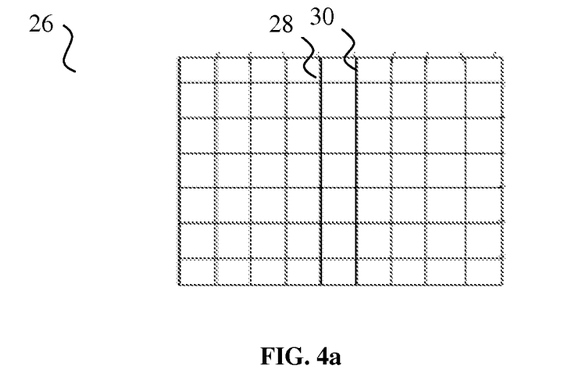
FIG. 4 shows another exemplary lateral flow assay device.
Figure 4B:
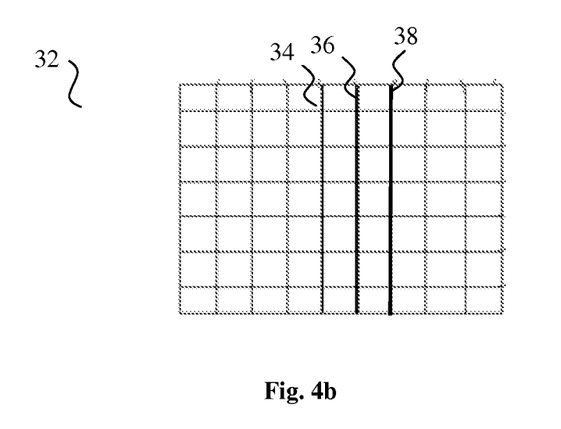

In some embodiments, the strands of the lateral flow assay device of the invention comprise more than one conducting material, wherein one of the conducting materials is used as a reference to calibrate signals arising from the other conducting materials. A useful reference conducting material is silver halide. FIG. 4a shows another exemplary lateral flow assay device 26 made by weaving a plurality of strands that comprises a working electrode and a reference electrode, wherein the working electrode 28 of the lateral flow assay device is made by coating one strand with a conducting material and a diagnostic material while the reference electrode 30 is made by coating another strand with a reference conducting material. FIG. 4b shows yet another exemplary lateral flow assay device 32 made by weaving a plurality of strands that comprises a working electrode, a reference electrode and a counter-electrode, wherein the working electrode 34 is made by coating one strand with a conducting material and a diagnostic material (i.e. enzyme and mediator in one instance, or enzyme alone in another instance), the reference electrode 36 is made by coating another strand with a reference conducting material and the counter electrode 38 is made by coating yet another strand with a conducting material.

Methods of coating are known and may include, for example, dip coating. In one embodiment, the fabric strand is first coated with the conducting material and then coated strand is used for weaving to make the lateral flow assay device. Alternately, the conducting material is printed onto the woven strands to make the lateral flow assay device. Other techniques will become obvious to one skilled in the art and is contemplated to be within the scope of the invention.

The coating is done such that the final fabric strand is rendered predefined properties. Useful properties that define the fabric include for example, resistance, tensile strength and so on, and combinations thereof. In one embodiment, the resistance of the working electrode is maintained less than about 1000 ohms/cm. In other embodiments, the resistance of the counter electrode is maintained less than about 1000 ohms/cm. In further embodiments, the fabric is coated with a diagnostic material is present at a suitable concentration that allows for measurable output. For example, when the diagnostic material is an enzyme such as glucose oxidase, it may be at least about 1 Unit per active length. Active length as used herein refers to the length of the testing zone of the lateral flow assay device.

In further embodiments, the strands of the lateral flow assay device may also be coated with other conducting material without any of the reagents, antibodies, antigens, or the like. In such instances, such strands may also be referred to as counter electrodes. Counter electrode when present generally includes only the strand coated with conducting ink and is generally used as a reference point for maintaining a constant potential to improve accuracy of readings.

The lateral flow assay device of the invention may further comprise colorants, emollients, other additives for various purposes, along with those mentioned herein. These additives may be for cosmetic purposes, to provide extra features, or add greater functionality to the existing lateral flow assay device. Further, the lateral flow assay device of the invention may be mounted onto a substrate. The substrate may be present to provide strength and mechanical integrity to the device. The substrate may be chosen from any number of strong materials known to those skilled in the art, and may include, for example, metal backing such as steel, iron, titanium, alloys, and the like, plastics such as poly(methyl methacrylate), polystyrene, polyethylene, polypropylene, and the like, cardboard, wood, and others, and combinations thereof.

The lateral flow assay device of the invention may further be encased in a suitable enclosure to protect it from environmental factors, such as handling during transportation, sunlight, moisture, humidity, and so on. In such instances, the enclosure may be designed in such a way that it can be opened to allow access to the device. Alternately, the enclosure may be present in such a way that there is an opening only for the sample introduction, so that the rest of the device is totally enclosed even during operation. Enclosures suitable for the device may have propertises such as transparency, strength, water resistance, moldability, and the like. Some useful materials that can perform well as enclosures for the device may include, but not limited to, glass, plastics such as poly(methyl methacrylate), polystyrene, polyethylene, polypropylene, and the like.

The invention as described herein provides weaving as an alternate manufacturing technology for the manufacture of fabric-based lateral flow assay devices that may also be referred to as 'fab chips'. Such devices may be reusable type or may be a single-use, disposable device. Fabric weaving is an art that has developed to a very high degree of skill in many parts of the world, and intricate patterns whose dimensions are limited only to the thickness of an individual thread may be woven in a highly parallelized manner. This technique is capable of being adapted for the manufacture of the devices of the invention in a facile manner. By weaving together strands of fibers along with fibers that are coated with reagents, it is possible to manufacture a very large number of diagnostic devices, which are capable of single-plexing and multiplexing. This will result in the ability to actually fabricate an entire diagnostic device using only a loom. This provides a great advantage over the existing techniques which uses different manufacturing methods for various parts of the diagnostic device, thus complicating the process. Further, unlike the currently commercially available diagnostic devices, such as the paper-based devices which require different materials to function as the conjugation pad, absorption pad and sample delivery pad, the invention provides a single uniform manufacturing process to make the lateral flow assay device.

During manufacture, a large strip of the lateral flow assay device of the invention may be made and subsequently, smaller strips may be cut, which are then taken for further processing, such as gluing onto a substrate, enclosing in a housing, and the like. The nature of the manufacturing process and device qualities allow for the possibility of patterning complex fluid geometries using standard weaving techniques. Further, an input sample may be split into multiple branches using a combination of hydrophilic and hydrophobic yarn during the weaving step, thus enabling multiplexing of tests. In one exemplary embodiment, the cotton fabric is interwoven with silk such that the cotton thread is present 3 millimeters (3 mm) apart, in another embodiment, the cotton fabric is interwoven with silk such that the cotton thread is present 1 mm apart, and in yet another embodiment, the cotton fabric is interwoven with silk such that the cotton thread is present 5 mm apart. The cotton may then be coated with a combination of a mediator, conducting material and diagnostic material in any suitable order. Alternately, cotton that is already coated with the conducting material, diagnostic material and the mediator is used for the interweaving with silk-based matrix.

In a use case situation of the lateral flow assay device of the invention, sample that may or may not comprise one or more analyte is introduced into the device at a sample introduction zone. The sample is then allowed to flow through the device thus allowing it to come into contact with the diagnostic material in its path. Analyte, if present, reacts with the diagnostic material on the conducting yarn, causing a chemical reaction that generates an electron transfer. These electrons (sometimes through a mediator) generate an electrical signal. The electron transfer rate is correlated with the concentration of the analyte which can then be measured using known techniques. Without being bound to any theory, it is known that the amount of electrons transferred is proportional to the concentration of analyte. One skilled in the art will also recognize that devices described herein may be used as single-plex devices or multiplex devices, by selecting the appropriate one or more diagnostic materials and the electrode materials as described herein depending on the requirements. The flow of the sample is curbed when there are no more flow regions available. Such flow-stop regions may be engineered using known techniques, and may include, for example absorption pads, increased hydrophobic matrix regions, and so on.

The device of the invention may be used for any assays to be performed in a wide variety of applications. For example, in case of using the device of the invention for a label-free immunoassay wherein direct detection of analyte can be effected by the appropriate use of a specific binding reagent such as antibody, following which the detection can occur through any one of cyclic voltammetry, chronoamperometry, impedimtery, pulsed amperommetric detection, and the like, and combinations thereof. In another exemplary situation, in case of using the device of the invention for a sandwich immunoassay, sample for qualitative detection of antigen in the sample is introduced on to the sample port of the lateral flow assay device. After introduction, as the sample flows along the predefined path from proximal end to the distal end due to capillary action, it comes in contact with secondary reagent (detection antibody) first in the testing zone, as it is present upstream from the primary reagent (capture antibody). Analyte (antigen) if present, forms a first complex with secondary reagent. Following this, the flow of the solution comprising the first complex reaches the primary reagent (capture antibody) forming a second complex comprising the analyte, primary reagent and secondary reagent. The complex induces a change in the conductivity of the conducting material, which is then read out using appropriate electrical measurement means. In some instances, an electroactive material such as ferrocene may be linked through physical or chemical means to the secondary reagent. The electroactive material will serve to improve the output from the device. If the sample does not comprise the analyte, then the first complex and the second complex does not form, thus no change in the conductivity of the conducting material relative to control conditions is discernible, and the sample flows until it reaches the absorption port. The solution stops flow when there are no more flow regions remaining on the device.

Figure 5:
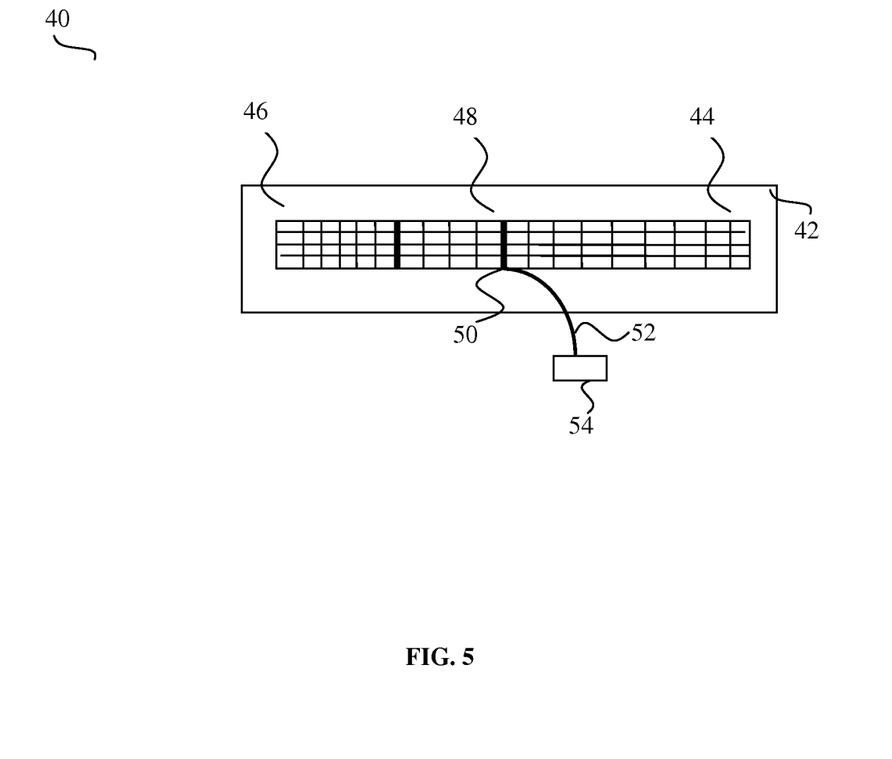
FIG. 5 shows an exemplary lateral flow assay system of the invention.

In another aspect, the invention provides a lateral flow assay system comprising: a lateral flow assay device as described hereon. FIG. 5 shows an exemplary lateral flow assay system of the invention, depicted by the numeral 40. The lateral flow device depicted by numeral 42 comprises a proximal end 44, a distal end 46 and a testing zone 48 intermediate between the proximal end and the distal end. The at least one strand of the fabric is coated with a conducting material in the testing zone, depicted by numeral 50. The strand coated with the conducting material is connected to at least one electrode 52, which in turn is connected to measurement means 54 to measure the output from the at least one electrode. Measured output from the at least one electrode incudes current, voltage, resistance, impedance, and the like, and combinations thereof. The lateral flow device may further comprise a reference material coated onto one of the strands to provide a reference output during test conditions.

EXAMPLE

A 500 micrometer (pm) cotton thread was obtained from a local commercial source and used as such. Silk thread with 22 Denier monofilament, bivoltine was obtained from Silk Touch, Bangalore, India. Carbon ink and Ag/AgCl was purchased from Creative Materials, USA. Potassium Ferricyanide and Glucose Oxidase having a concentration of 192 U/mg was obtained from Sigma-Aldrich, USA. Water as used in the examples described herein means deionized water.

Figure 6:
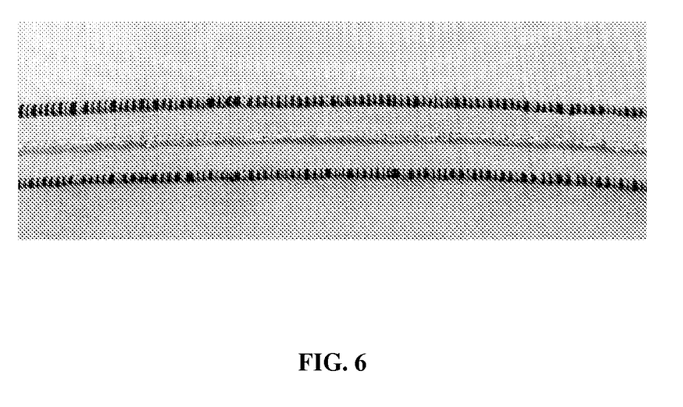
FIG. 6 shows an image of the woven fabric as embodied by Example.
Figure 7:
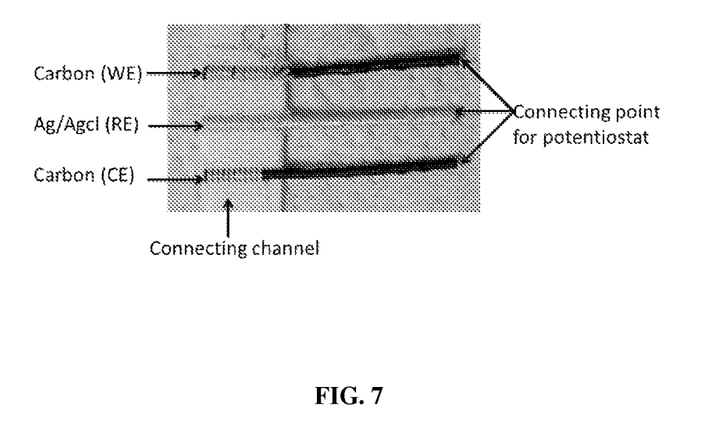
FIG. 7 shows a single strip cut from the woven fabric seen in FIG. 6 to form the lateral flow assay device.

Silk threads were converted into 4 ply 25 twist per inch (TPI) and then degummed using the procedure described in publication number WO2012/004635. All the coatings were achieved by dip coating technique. Working electrode was prepared by coating cotton thread with carbon ink and potassium ferricyanide followed by Glucose Oxidase. A range of concentrations of each component was used for testing purposes. Reference electrode was prepared by coating cotton with Ag/AgCl ink such the concentration of the ink gives rise to a resistance ranging from about 250-300 Ohm/cm. Counter electrode was prepared by coating carbon ink on the cotton thread. The appropriately coated cotton threads were woven along the weft direction with degummed silk such that the coated cotton was present at a distance of 3 mm intervals to make the working electrode, reference electrode and counter-electrode respectively for each device, wherein the degummed silk was used in the warp and weft direction. FIG. 6 shows an image of the lateral flow assay described here. A single strip about 4 mm wide containing three electrodes was then cut from the woven fabric shown and connections were made from the three electrodes to a potentiostat as shown in FIG. 7.

Figure 8:
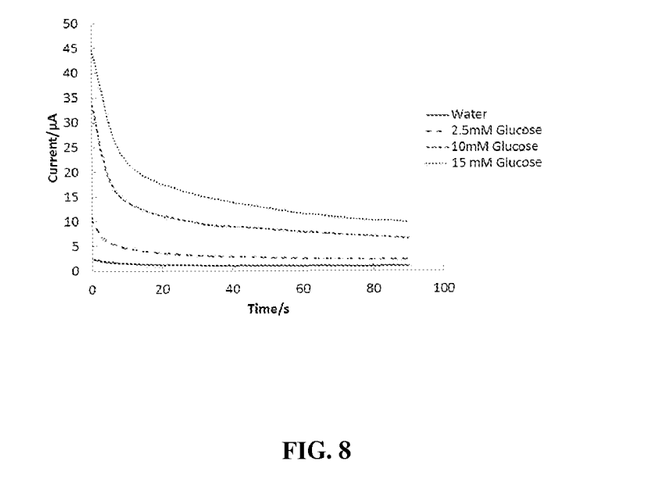
FIG. 8 shows amperometric profiles for samples containing different concentrations of glucose in phosphate buffered saline as measured by the lateral flow assay device of the invention.

Samples of water spiked with no glucose, 2.5 Mm, 10 mM glucose and 15 mM glucose were then used to test the performance of the lateral flow assay devices. The liquid solutions wetted the entire strip through capillary action after being input in the sample entry port and initiated a reaction at the working electrode surface which had been immobilized with enzyme. The redox reaction catalyzed by the Glucose Oxidase and mediated by Potassium Ferricyanide releases electrons to produce a current at the working electrode. A standard amperometric technique which applies a constant potential and then measures the current profile versus time was used. Data from different samples tested were plotted and shown in FIG. 8. The bottom line that remains unchanged over the entire period was obtained from water sample with no glucose, while the other curves are for aqueous glucose solutions having concentrations of 2.5 millimoles (mM), 10 mM and 15 mM respectively. It can be seen that current produced at the electrode is proportional to the concentration of glucose in the sample, while the control phosphate buffered saline having no glucose (PBS) gives a flat readout. This demonstrates that different concentrations of glucose can be detected by analyzing the data. It must be noted that any current value at a given time can be used for measurement and analysis purposes.

Figure 9:
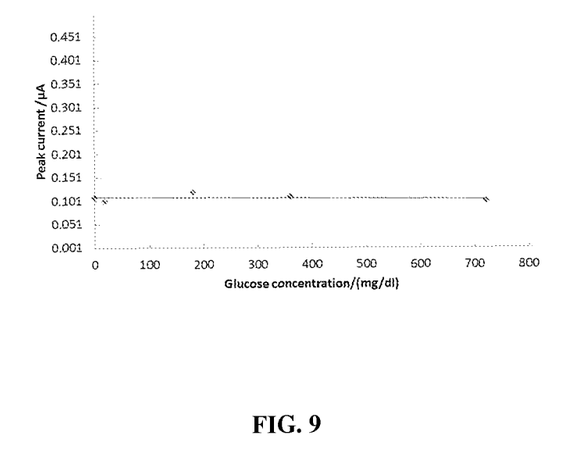
FIG. 9 shows a plot of the current output from a control lateral flow assay device for the different concentrations of the aqueous glucose solutions.
Figure 10:
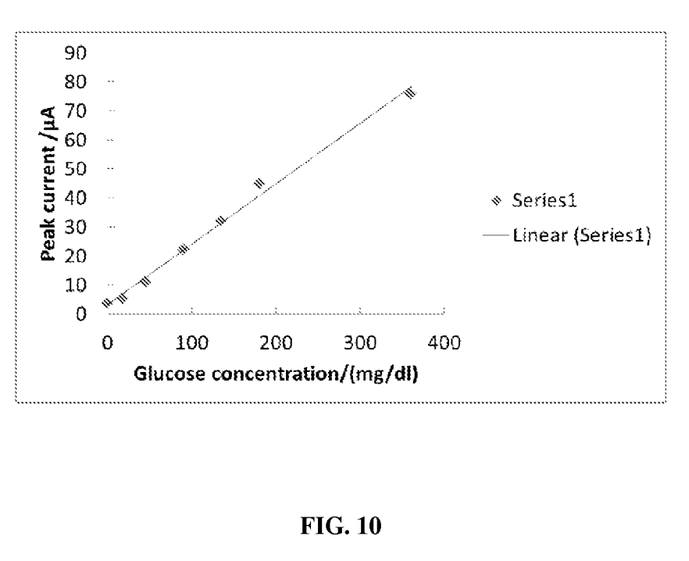
FIG. 10 shows a plot of peak current against glucose concentration as measured by a control lateral flow assay device.

A control lateral flow assay device comprising counter electrode, a reference electrode and another counter electrode was prepared. This device was subjected aqueous glucose solutions of various concentrations and the output current was measured, which is shown in FIG. 9. FIG. 10 shows a graph of the peak current (at time=0 seconds) versus glucose concentration. It can be seen that the peak output current is concentration independent when the diagnostic material glucose oxidase is absent in the control device.

A calibration curve was then obtained for the lateral flow assay device of the invention for a series of aqueous solutions comprising known concentrations of glucose. FIG. 11 shows a plot of the peak output current from the device for the different concentrations of the aqueous glucose solutions. It can be seen that a linear relationship in the concentration range shown here exists.

While only certain features of the invention have been illustrated and described herein, many modifications and changes will occur to those skilled in the art. It is, therefore, to be understood that the appended claims are intended to cover all such modifications and changes as fall within the true spirit of the invention.

We claim:

1. An electrochemical assay device comprising a fabric made of a plurality of strands interwoven together, wherein the fabric has a proximal end, a distal end and a testing zone intermediate between the proximal end and the distal end, and wherein the plurality of strands comprises:
    at least one conducting strand comprising a conducting material at least in the testing zone;
    at least one hydrophilic strand; and
    at least one hydrophobic strand, wherein the at least one hydrophobic strand is interwoven with the at least one conducting strand and the at least one hydrophilic strand to provide a patterned flow path.

2. The electrochemical assay device of claim 1, wherein the fabric comprises a sample introduction zone at the proximal end.

3. The electrochemical assay device of claim 1, wherein the at least one conducting strand of the fabric is made of fibers selected from a group comprising cotton, silk, viscose, polypropylene, nylon, or combinations thereof, and wherein the at least one conducting strand is coated with the conducting material in the testing zone.

4. The electrochemical assay device of claim 3, wherein the conducting material is selected from a group comprising carbon ink, gold, platinum, or combinations thereof.

5. The electrochemical assay device of claim 1, wherein the at least one conducting strand is coated with a mediator.

6. The electrochemical assay device of claim 5, wherein the mediator is potassium ferricyanide.

7. The electrochemical assay device of claim 5, wherein the concentration of the conducting material and the mediator is such that the resistance of the at least one conducting strand is less than about 1000 ohms/cm.

8. The electrochemical assay device of claim 1, wherein the plurality of strands further comprise at least one strand coated with a reference conducting material in the testing zone to form a reference electrode.

9. The electrochemical assay device of claim 8, wherein the reference conducting material is a silver/silver halide ink.

10. The electrochemical assay device of claim 1, wherein the plurality of strands further comprise at least one strand coated with the conducting material to form a counter electrode, wherein the concentration of the conducting material is such that the resistance of the counter electrode is less than about 1000 ohms/cm.

11. The electrochemical assay device of claim 1 further comprising a substrate to support the fabric.

12. The electrochemical assay device of claim 11, wherein the substrate is made of a material selected from a group comprising plastic, metal, wood, cardboard, or combinations thereof.

13. The electrochemical assay device of claim 1 further comprising a housing to house the fabric.

14. The electrochemical assay device of claim 13, wherein the housing comprises at least one of a sample introduction port, a transparent viewing port, or combinations thereof.

15. The electrochemical assay device of claim 13, wherein the housing is made of plastic, metal, wood, cardboard, or combinations thereof.

16. The electrochemical assay device of claim 1, wherein the at least one conducting strand is coated with a diagnostic material to provide a working electrode.

17. The electrochemical assay device of claim 16, wherein the diagnostic material is present at a concentration of at least about 1 Unit per active length of the working electrode.

18. The electrochemical assay device of claim 16, wherein the diagnostic material is glucose oxidase.

19. The electrochemical assay device of claim 1, wherein the at least one conducting strand is made of carbon fiber.

* * * * *